United States Patent
Ogawa

(10) Patent No.: US 9,788,711 B2
(45) Date of Patent: Oct. 17, 2017

(54) ENDOSCOPE REPROCESSOR

(71) Applicant: OLYMPUS CORPORATION, Tokyo (JP)

(72) Inventor: Akihisa Ogawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/195,010

(22) Filed: Jun. 28, 2016

(65) Prior Publication Data

US 2016/0302654 A1 Oct. 20, 2016

Related U.S. Application Data

(63) Continuation of application No. PCT/JP2015/077444, filed on Sep. 29, 2015.

(30) Foreign Application Priority Data

Nov. 17, 2014 (JP) .................... 2014-232937

(51) Int. Cl.
*A61B 1/12* (2006.01)
*A61L 2/18* (2006.01)
(Continued)

(52) U.S. Cl.
CPC ............... *A61B 1/123* (2013.01); *A61B 1/12* (2013.01); *A61L 2/18* (2013.01); *A61L 2/24* (2013.01);
(Continued)

(58) Field of Classification Search
CPC ........................... A61B 1/123; A61L 2202/24
See application file for complete search history.

(56) References Cited

U.S. PATENT DOCUMENTS 6,106,691 A * 8/2000 Nakamura ............... A61L 2/18
134/26
6,203,767 B1 3/2001 Leasko
(Continued)

FOREIGN PATENT DOCUMENTS

EP 1757313 A1 2/2007
JP H01-094822 A 4/1989
(Continued)

OTHER PUBLICATIONS

Rutala, W.A., Weber, D.J. and the Healthcare Infection Control Practices Advisory Committee (HICPAC), Guideline for Disinfection and Sterilization in a Healthcare Facilities, 2008, Nov. 2008, pp. 1-158, retrieved from the Internet: URL:http: www.cdc.gov/hicpac/pdf/guidelines/Disinfection_Nov_2008.pdf. [retreived on Jan. 1, 2015].

(Continued)

*Primary Examiner* — Jason Ko
*Assistant Examiner* — Spencer Bell
(74) *Attorney, Agent, or Firm* — Scully, Scott, Murphy & Presser, P.C.

(57) ABSTRACT

An endoscope reprocessor includes: an endoscope housing portion; a medicinal solution tank in which a medicinal solution is stored; a medicinal solution transfer portion that transfers the medicinal solution from the medicinal solution tank to the endoscope housing portion; a comparison portion that compares the concentration of the medicinal solution and a first reference concentration; a first adjustment portion that increases a reaction rate of the medicinal solution in a state in which the concentration of the medicinal solution is lower than the first reference concentration; and a control portion to which the comparison portion and the first adjustment portion are connected, and which drives the first adjustment portion in a case where the comparison portion (Continued)

determines that the concentration of the medicinal solution is lower than the first reference concentration.

3 Claims, 14 Drawing Sheets

(51) Int. Cl.
*A61L 2/24* (2006.01)
*B08B 3/10* (2006.01)
*B08B 3/08* (2006.01)
*B08B 9/032* (2006.01)
*B08B 9/023* (2006.01)

(52) U.S. Cl.
CPC .............. *B08B 3/08* (2013.01); *B08B 3/10* (2013.01); *B08B 3/102* (2013.01); *B08B 9/023* (2013.01); *B08B 9/0325* (2013.01); *A61L 2202/17* (2013.01); *A61L 2202/24* (2013.01)

(56) References Cited

U.S. PATENT DOCUMENTS

| 2006/0219261 A1* | 10/2006 | Lin .................... A61B 1/00057 134/18 |
| 2007/0048183 A1 | 3/2007 | Nguyen et al. |
| 2010/0004510 A1* | 1/2010 | Kuroshima ............ A61B 1/012 600/158 |

FOREIGN PATENT DOCUMENTS

| JP | 2007-061611 A | 3/2007 |
| JP | 2010-057752 A | 3/2010 |
| JP | 2010-057792 A | 3/2010 |
| WO | 2009/032644 A2 | 3/2009 |

OTHER PUBLICATIONS

Partial Supplementary European Search Report dated Aug. 9, 2017 in European Patent Application No. 15 86 1418.0.

* cited by examiner

FIG. 2

| DISINFECTING PARAMETERS | EFFECTIVE CONCENTRATION LOWER LIMIT | TEMPERATURE | TIME |
|---|---|---|---|
| FIRST EFFECT PARAMETERS | B ppm | D°C | F min |
| SECOND EFFECT PARAMETERS | C ppm | E°C | F min |

| DISINFECTING PARAMETERS | EFFECTIVE CONCENTRATION LOWER LIMIT | AIR PRESSURE | TEMPERATURE | TIME |
|---|---|---|---|---|
| FIRST EFFECT PARAMETERS | B ppm | NORMAL PRESSURE | D°C | Fmin |
| SECOND EFFECT PARAMETERS | C ppm | NORMAL PRESSURE - Hhp | D°C | Fmin |

| DISINFECTING PARAMETERS | EFFECTIVE CONCENTRATION LOWER LIMIT | VIBRATION | TEMPERATURE | TIME |
|---|---|---|---|---|
| FIRST EFFECT PARAMETERS | B ppm | NO | D°C | Fmin |
| SECOND EFFECT PARAMETERS | C ppm | YES | D°C | Fmin |

| DISINFECTING PARAMETERS | EFFECTIVE CONCENTRATION LOWER LIMIT | TIME | TEMPERATURE |
|---|---|---|---|
| FIRST EFFECT PARAMETERS | B ppm | Fmin | D°C |
| SECOND EFFECT PARAMETERS | C ppm | Gmin | D°C |

C<B , G>F

ENDOSCOPE REPROCESSOR

CROSS REFERENCE TO RELATED APPLICATION

This application is a continuation application of PCT/JP2015/077444 filed on Sep. 29, 2015 and claims benefit of Japanese Application No. 2014-232937 filed in Japan on Nov. 17, 2014, the entire contents of which are incorporated herein by this reference.

BACKGROUND OF THE INVENTION

1. Field of the Invention

The present invention relates to an endoscope reprocessor having an endoscope housing portion in which an endoscope is housed and in which the endoscope is immersed in a medicinal solution.

2. Description of the Related Art

Medicinal solution treatment of an endoscope using an endoscope reprocessor is performed by supplying a medicinal solution that is stored in a medicinal solution tank to an endoscope housing portion through a medicinal solution conduit accompanying driving of a medicinal solution transfer portion, so that an endoscope comes in contact with the medicinal solution at a preset temperature and for a predetermined time period in the endoscope housing portion.

Controlling the concentration of the medicinal solution so that the medicinal efficacy is not lowered is important to reliably perform medicinal solution treatment of an endoscope. The reason is because there are some medicinal solutions for which the concentration decreases from an initial concentration due to repeated use or natural deterioration. Hence, checking of the medicinal solution concentration is generally performed each time a medicinal solution treatment process is performed on an endoscope.

Various techniques are known for checking a medicinal solution concentration. Examples of such techniques include techniques that check whether the concentration of a medicinal solution is equal to or greater than an effective concentration by sampling a medicinal solution from a medicinal solution sampling port provided at a position partway along the medicinal solution conduit, and then immersing a test paper in the medicinal solution and observing a change in the color of the test paper, or by coloring the medicinal solution after sampling, and measuring the transmittance of light according to the shading of the color using an absorptiometer to convert the concentration of the medicinal solution into a numerical value.

Further, in Japanese Patent Application Laid-Open Publication No. 2010-57792, an endoscope cleaning/disinfecting apparatus is disclosed that, by providing a medicinal solution concentration sensor in a medicinal solution tank, can automatically check whether the concentration of a medicinal solution is equal to or greater than an effective concentration without separately sampling the medicinal solution.

Japanese Patent Application Laid-Open Publication No. 2010-57792 also discloses a configuration that, in a case where a medicinal solution concentration that is detected by the concentration sensor is less than an effective concentration lower limit, locks a top cover of the endoscope cleaning/disinfecting apparatus to prevent an endoscope that was subjected to medicinal solution treatment by a medicinal solution whose concentration is less than the effective concentration lower limit being taken out from the endoscope housing portion, and urges the operator to replace the medicinal solution.

SUMMARY OF THE INVENTION

An endoscope reprocessor according to one aspect of the present invention includes: an endoscope housing portion in which an endoscope is housed; a medicinal solution tank that is communicated with the endoscope housing portion and in which a medicinal solution is stored; a medicinal solution transfer portion that transfers the medicinal solution from the medicinal solution tank to the endoscope housing portion; a comparison portion that compares a concentration of the medicinal solution and a first reference concentration; a first adjustment portion that increases a reaction rate of the medicinal solution in a state in which the concentration of the medicinal solution is lower than the first reference concentration; and a control portion to which the comparison portion and the first adjustment portion are connected, and which drives the first adjustment portion in a case where the comparison portion determines that the concentration of the medicinal solution is lower than the first reference concentration.

BRIEF DESCRIPTION OF THE DRAWINGS

FIG. 2 is a chart showing disinfecting parameters that are stored in a storage portion of the endoscope cleaning/disinfecting apparatus shown in FIG. 1;

FIG. 7 is a chart showing disinfecting parameters that are stored in a storage portion of the endoscope cleaning/disinfecting apparatus shown in FIG. 6;

FIG. 11 is a chart showing disinfecting parameters that are stored in a storage portion of the endoscope cleaning/disinfecting apparatus shown in FIG. 10;

FIG. 12 is a chart showing disinfecting parameters that are stored in a storage portion of an endoscope cleaning/disinfecting apparatus of a second embodiment;

DETAILED DESCRIPTION OF THE PREFERRED EMBODIMENTS

Embodiments of the present invention are described hereunder with reference to the accompanying drawings. Note that the drawings are schematic ones in which the relationship between the thickness and width of each member, the thickness ratios of the respective members and the like are different from those of actual members. Naturally, the drawings include portions in which the dimensional relationships and ratios are different from one another among the drawings. The endoscope reprocessor of the present invention is an apparatus that performs a regeneration treatment on an endoscope. The regeneration treatment referred to here is not particularly limited, and may be any one of, or a combination of any two or more of, the following: a rinsing treatment using water, a cleaning treatment that removes dirt such as organic matter, a disinfecting treatment that nullifies predetermined microorganisms, and a sterilization treatment that eliminates or kills all microorganisms. Note that the following embodiments are described by taking an endoscope cleaning/disinfecting apparatus as an example of the endoscope reprocessor. Further, a disinfectant solution is taken as an example for describing a medicinal solution that is used in medicinal solution treatment of an endoscope in the endoscope cleaning/disinfecting apparatus.

First Embodiment

Figure 1:
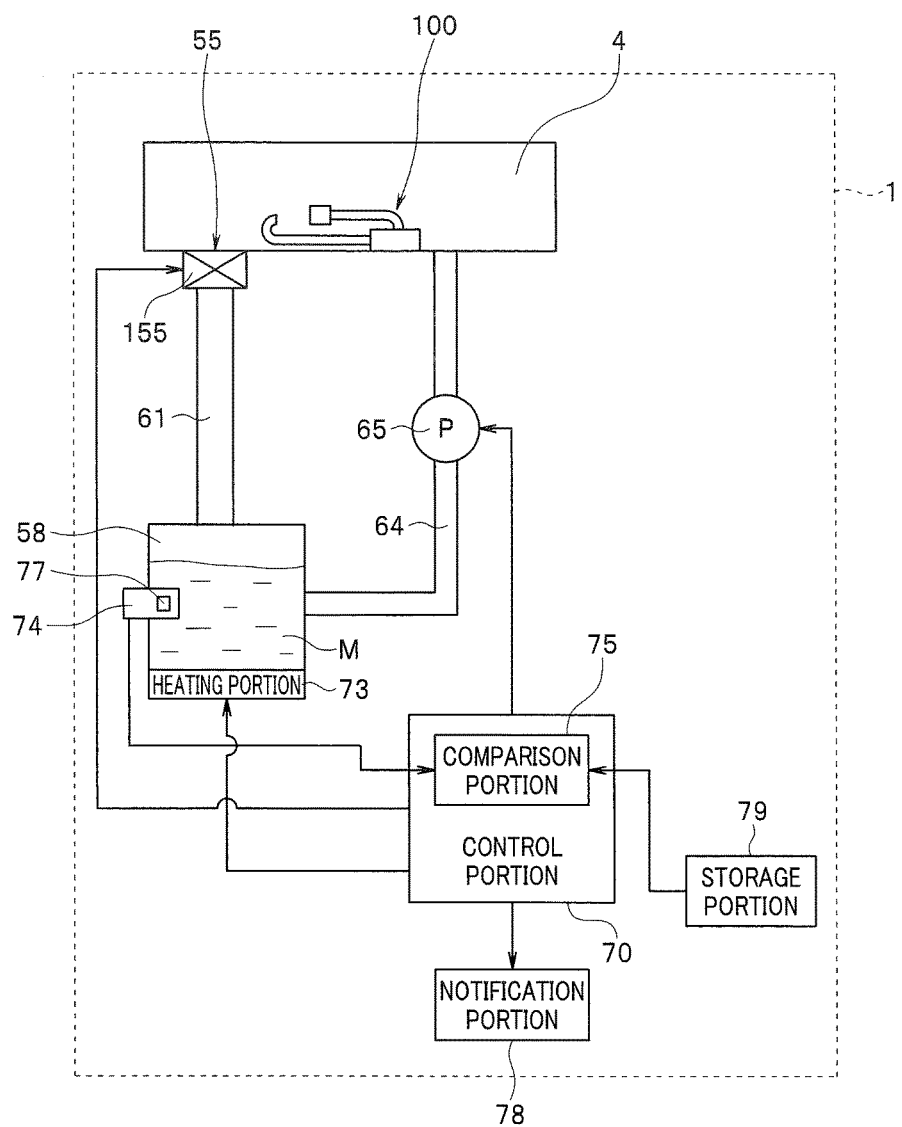
FIG. 1 is a view that schematically illustrates the configuration of an endoscope cleaning/disinfecting apparatus of a first embodiment.

FIG. 1 is a view that schematically illustrates the configuration of an endoscope cleaning/disinfecting apparatus of the present embodiment. FIG. 2 is a chart showing disinfecting parameters stored in a storage portion of the endoscope cleaning/disinfecting apparatus shown in FIG. 1.

As shown in FIG. 1, a principal portion of the endoscope cleaning/disinfecting apparatus 1 is constituted by an endoscope housing portion 4, a medicinal solution tank 58, a medicinal solution transfer portion 65, a first adjustment portion 73, a concentration detection portion 74, a control portion 70 including a comparison portion 75, and a storage portion 79.

The endoscope housing portion 4 is a portion in which an endoscope 100 to be treated with a disinfectant solution is housed. In a disinfection process, the endoscope 100 is immersed in a disinfectant solution M that is stored in the endoscope housing portion 4.

Note that a mixed solution in which peracetic acid and a buffer agent are mixed that is diluted to a predetermined initial concentration A ppm with water may be mentioned as an example of the disinfectant solution M.

A known disinfectant solution other than peracetic acid can also be applied as the disinfectant solution M. For example, a solution in which the stock solution itself is diluted to a predetermined initial concentration A ppm with water without using a buffer agent may be applied as the disinfectant solution M, such as a solution obtained by diluting glutaraldehyde to the predetermined initial concentration A ppm with water.

In addition, the disinfectant solution M has a plurality of effective concentration lower limits, and has disinfecting parameters with respect to which a disinfecting effect is confirmed for the respective effective concentration lower limits.

Specifically, as shown in FIG. 2, the disinfectant solution M includes first effect parameters and second effect parameters. The first effect parameters include a first reference concentration (effective concentration lower limit) B ppm that is lower than the initial concentration A ppm (B<A), a disinfectant solution temperature D° C., and an immersion time Fmin. The second effect parameters include a second reference concentration (effective concentration lower limit) C ppm that is lower than the effective concentration lower limit B ppm (C<B), a disinfectant solution temperature E° C. (E>D), and an immersion time Fmin, and exert a disinfectant solution effect (medicinal efficacy) that is equal to that of the first effect parameters.

Note that the first reference concentration B ppm is a concentration of the disinfectant solution M that is taken as the conventional effective concentration lower limit.

As described above, the concentration of the disinfectant solution M decreases accompanying usage or due to natural deterioration.

The medicinal solution tank 58 is communicated with the endoscope housing portion 4 through a medicinal solution recovery conduit 61 and a medicinal solution conduit 64, and the disinfectant solution M is stored in the medicinal solution tank 58.

Specifically, the disinfectant solution M diluted to the initial concentration A ppm with water, that is supplied via a medicinal solution supply conduit 62 (see FIG. 16) from medicinal solution bottles 12a and 12b (both illustrated in FIG. 15) that are placed in a disinfectant solution tray 12 that is described later, and the disinfectant solution M having a concentration from the initial concentration A ppm to the second reference concentration C ppm that is recovered through the medicinal solution recovery conduit 61 from the endoscope housing portion 4 are stored.

The medicinal solution recovery conduit 61 is a conduit that recovers a medicinal solution from the endoscope housing portion 4 to the medicinal solution tank 58 as a result of a valve element 155 of a discharge port 55 provided in the endoscope housing portion 4 being opened by driving control executed by the control portion 70.

Note that, when a disinfection process in which the endoscope 100 is immersed in the disinfectant solution M in the endoscope housing portion 4 is being performed, the valve element 155 is closed by driving control executed by the control portion 70.

The medicinal solution conduit 64 is a conduit that transfers disinfectant solution M inside the medicinal solution tank 58 to the endoscope housing portion 4 based on driving of the medicinal solution transfer portion 65.

The medicinal solution transfer portion 65 is a portion that, based on driving control executed by the control portion 70, transfers the disinfectant solution M from the medicinal solution tank 58 to the endoscope housing portion 4, and is constituted by, for example, a pump.

The first adjustment portion 73 is provided in the medicinal solution tank 58, and is constituted by a component that increases the reaction rate of the disinfectant solution M based on driving control executed by the control portion 70. For example, the first adjustment portion 73 is constituted by a heating portion that increases the medicinal efficacy of the disinfectant solution M by raising the temperature of the disinfectant solution to a predetermined temperature.

Note that, a configuration may also be adopted in which the first adjustment portion 73 is provided in the endoscope housing portion 4, the medicinal solution recovery conduit 61, or the medicinal solution conduit 64 or the like, and the present invention is not limited to a configuration in which the first adjustment portion 73 is provided in the medicinal solution tank 58. Hereunder, in the present embodiment, the heating portion is denoted by reference numeral 73.

The concentration detection portion 74 is provided in the medicinal solution tank 58 and connected to the comparison portion 75, and is constituted by, for example, a sensor that detects the concentration of the disinfectant solution M. Note that, with respect to the concentration detection portion 74 also, a configuration may be adopted in which the concentration detection portion 74 is provided in the endoscope housing portion 4, the medicinal solution recovery conduit 61, or the medicinal solution conduit 64 or the like, and a location at which the concentration detection portion 74 is provided is not limited to the medicinal solution tank 58.

A thermometer 77 that measures the temperature of the disinfectant solution M is provided in the concentration detection portion 74. Note that the thermometer 77 may also be provided separately from the concentration detection portion 74.

The comparison portion 75 is a portion into which the concentration of the disinfectant solution M is inputted through the concentration detection portion 74, and which compares the concentration of the disinfectant solution M that is detected by the concentration detection portion 74 with the first reference concentration B and the second reference concentration C that are illustrated in FIG. 2. Note that the comparison portion 75 may also be provided separately from the control portion 70.

The control portion 70 is a portion that performs control to open/close the valve element 155 provided in the discharge port 55, driving control of the medicinal solution transfer portion 65, driving control of the heating portion 73, and driving control of a notification portion 78. The medicinal solution transfer portion 65, the heating portion 73, the comparison portion 75, the notification portion 78 and the storage portion 79 are connected to the control portion 70.

If the comparison portion 75 determines that the concentration of the disinfectant solution M is lower than the first reference concentration B, the control portion 70 executes driving control of the heating portion 73.

In addition, if the comparison portion 75 determines that the concentration of the disinfectant solution M is lower than the second reference concentration C, the control portion 70 executes driving control of the notification portion 78.

The notification portion 78 is a portion that notifies a warning to the operator. Note that a sound or a display using a main operation panel 25 that is described later (see FIG. 14) or the like may be mentioned as examples of a warning.

As shown in FIG. 2, the above described disinfecting parameters are stored in the storage portion 79.

Figure 3:
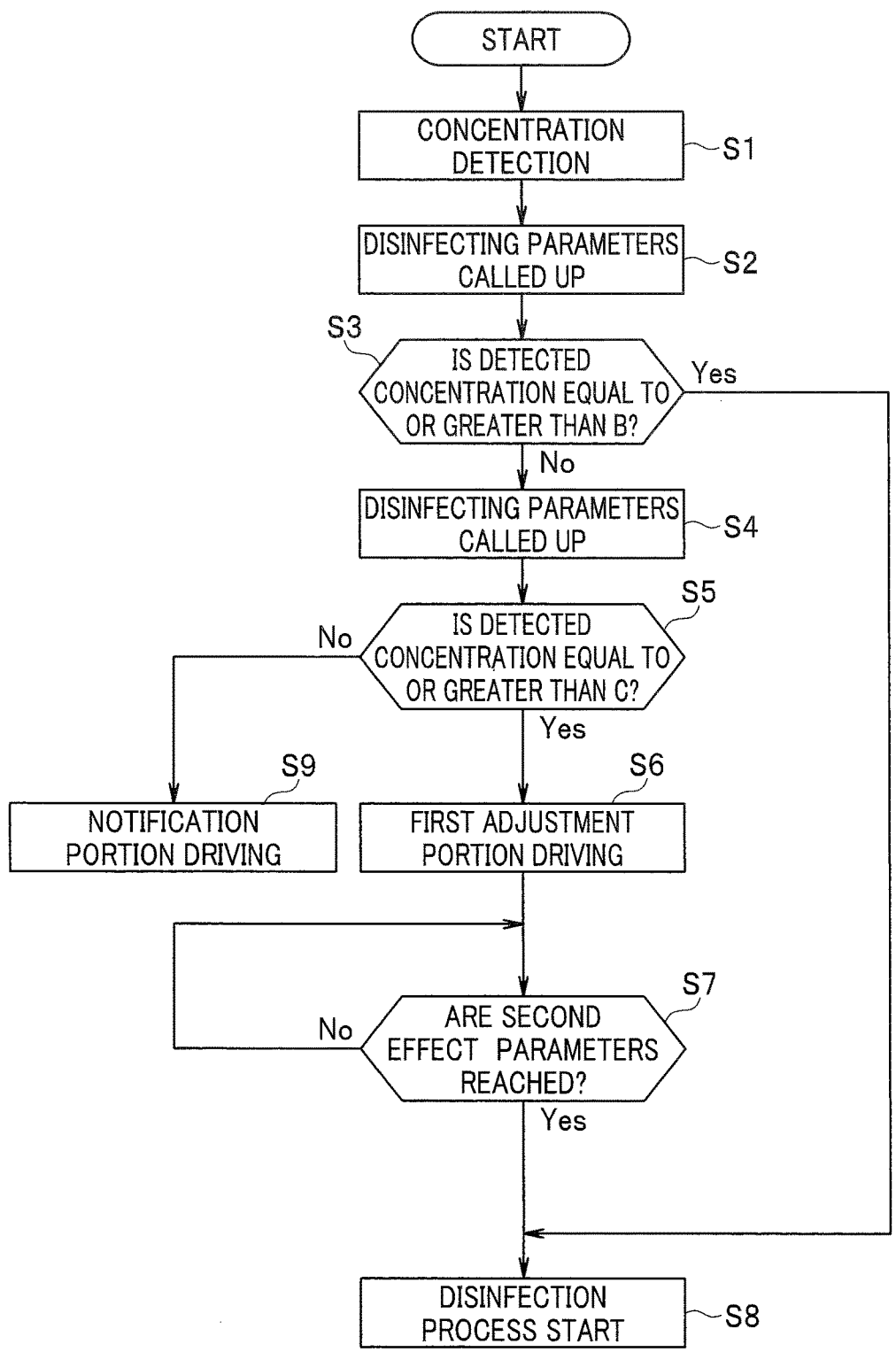
FIG. 3 is a flowchart illustrating various kinds of driving control executed by a control portion when detecting a concentration of a disinfectant solution in the endoscope cleaning/disinfecting apparatus shown in FIG. 1.

Next, operations in the present embodiment are described using FIG. 3. FIG. 3 is a flowchart illustrating various kinds of driving control of the control portion that are executed when detecting the concentration of a disinfectant solution in the endoscope cleaning/disinfecting apparatus shown in FIG. 1.

First, when performing disinfecting treatment of the endoscope 100 that is housed in the endoscope housing portion 4, as shown in FIG. 3, in step S1 the control portion 70 detects the concentration of the disinfectant solution M in the medicinal solution tank 58 using the concentration detection portion 74.

Next, in step S2, the control portion 70 calls up disinfecting parameters from the storage portion 79, and in step S3 the control portion 70 determines whether the detected concentration of the disinfectant solution M is equal to or greater than the first reference concentration B ppm by performing a comparison using the comparison portion 75.

If the detected concentration of the disinfectant solution M is equal to or greater than the first reference concentration B ppm, the control portion 70 jumps to step S8. In step S8, the control portion 70 starts a disinfection process by executing driving control of the medicinal solution transfer portion 65 to supply the disinfectant solution M inside the medicinal solution tank 58 to the endoscope housing portion 4 through the medicinal solution conduit 64 to immerse the endoscope 100 in the endoscope housing portion 4 in the disinfectant solution M for the immersion time of Fmin.

Note that, needless to say that at this time the temperature of the disinfectant solution M is the predetermined temperature D° C. to which the disinfectant solution M is heated by the heating portion 73.

If the detected concentration of the disinfectant solution M is less than the first reference concentration B ppm, the control portion 70 transitions to step S4 in which the control portion 70 again calls up disinfecting parameters from the storage portion 79.

Subsequently, in step S5, the control portion 70 determines whether the detected concentration of the disinfectant solution M is equal to or greater than the second reference concentration C ppm by performing a comparison using the comparison portion 75.

If the detected concentration of the disinfectant solution M is less than the second reference concentration C, the control portion 70 branches to step S9. In step S9, on the basis that the disinfectant solution M has no medicinal efficacy, the control portion 70 executes driving control of the notification portion 78 to prompt the operator to replace the disinfectant solution M.

Note that, at this time, the control portion 70 may also perform control that stops operation of the endoscope cleaning/disinfecting apparatus 1.

If the detected concentration of the disinfectant solution M is equal to or greater than the second reference concentration C, the control portion 70 transitions to step S6 in which the control portion 70 performs driving control of the heating portion 73 to heat the disinfectant solution M.

Note that, as shown in step S7, heating of the disinfectant solution M is performed until the disinfectant solution M reaches the second effect parameters, that is, until the temperature of the disinfectant solution M reaches the temperature E° C. The temperature of the disinfectant solution M is measured by the thermometer 77 of the concentration detection portion 74.

Finally, in step S7, if the concentration of the disinfectant solution M is equal to or greater than the second reference concentration C ppm and the temperature of the disinfectant solution M has reached the temperature E° C. so that the second effect parameters are thus satisfied, the control portion 70 determines that the disinfectant solution M has a medicinal efficacy that is equal to the medicinal efficacy of the first effect parameters, and therefore transitions to step S8 to start the above described disinfection process.

Note that, checking of the concentration of the disinfectant solution M by the control portion 70 illustrated in FIG. 3 that is described above is performed each time a disinfection process is performed on the endoscope 100.

Thus, in the present embodiment the endoscope cleaning/disinfecting apparatus 1 has the heating portion 73 that raises the temperature of the disinfectant solution M to a predetermined temperature, and in a case where the comparison portion 75 determines that the concentration of the disinfectant solution M is lower than the first reference concentration (effective concentration lower limit) B ppm of the first effect parameters, the control portion 70 executes driving control of the heating portion 73 to heat the disinfectant solution M to the temperature E° C. that is higher than the temperature D° C. of the first effect parameters.

By this means, although conventionally it would be necessary to perform an operation to replace the disinfectant solution M in a case where the concentration of the disinfectant solution M is less than B ppm, according to the present embodiment, by the control portion 70 executing control to heat the disinfectant solution M to the temperature E° C. to satisfy the second effect parameters, the life of the disinfectant solution M can be prolonged by temporarily using the disinfectant solution M having the concentration C ppm that is lower than B ppm without lowering the medicinal efficacy of the disinfectant solution M from that of the first effect parameters, and hence the operator can perform an operation to replace the disinfectant solution M at a favorable timing in terms of work efficiency.

Furthermore, although conventionally there are cases in which, to prioritize work efficiency, the medicinal solution is discarded at a set time even if the concentration of the medicinal solution is equal to or greater than the effective concentration, the present invention can suppress the occurrence of such wastefulness.

As described above, the endoscope cleaning/disinfecting apparatus 1 can be provided that has a configuration that can be temporarily used for medicinal solution treatment of the endoscope 100 without lowering the medicinal efficacy even in a case where the concentration of the disinfectant solution is less than the first reference concentration.

Figure 4:
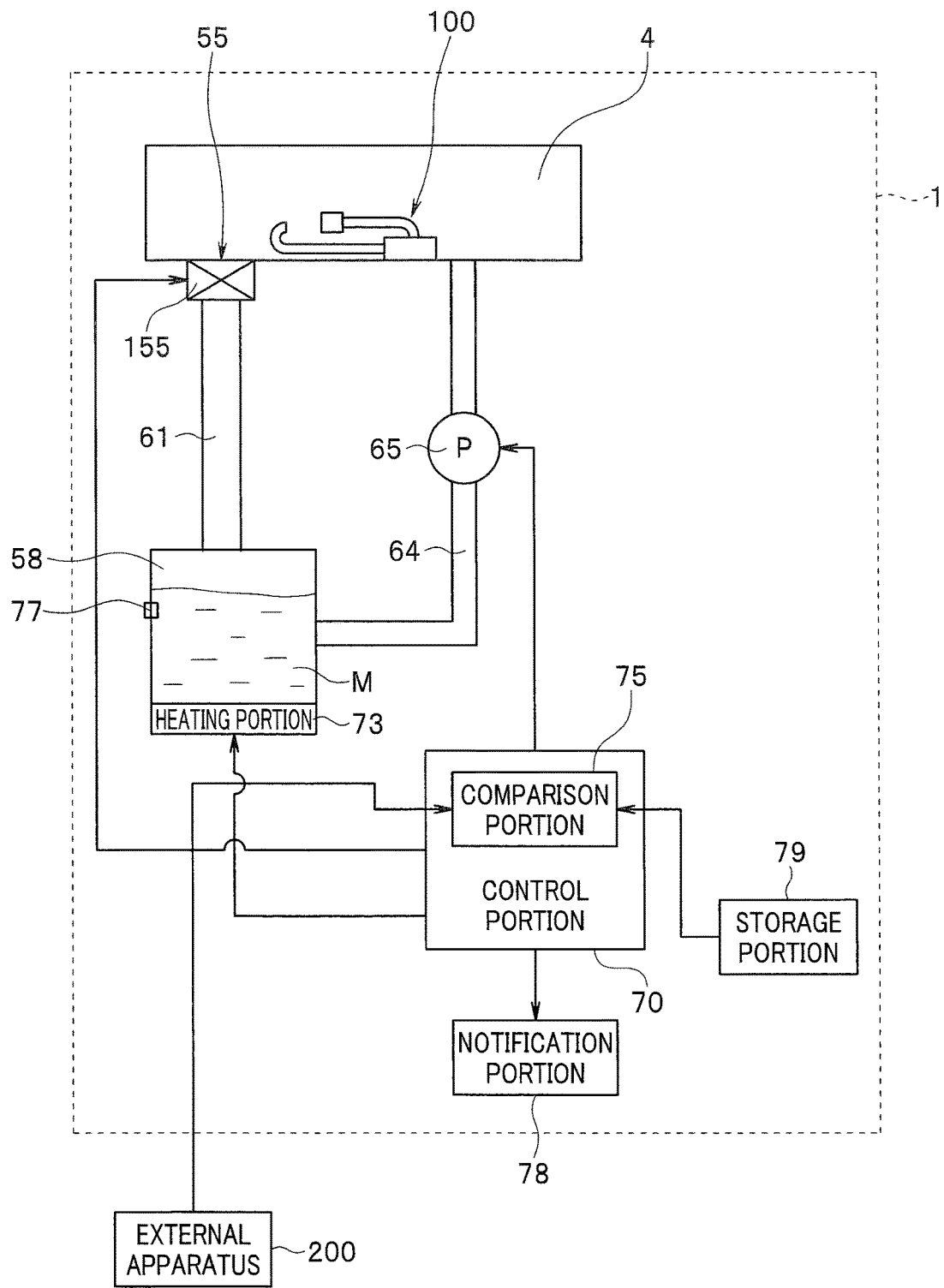
FIG. 4 is a view that schematically illustrates a modification of the configuration of the endoscope cleaning/disinfecting apparatus in which detection of the concentration of a disinfectant solution is performed by an external apparatus, and a detected concentration is inputted to a comparison portion from the external apparatus.
Figure 5:
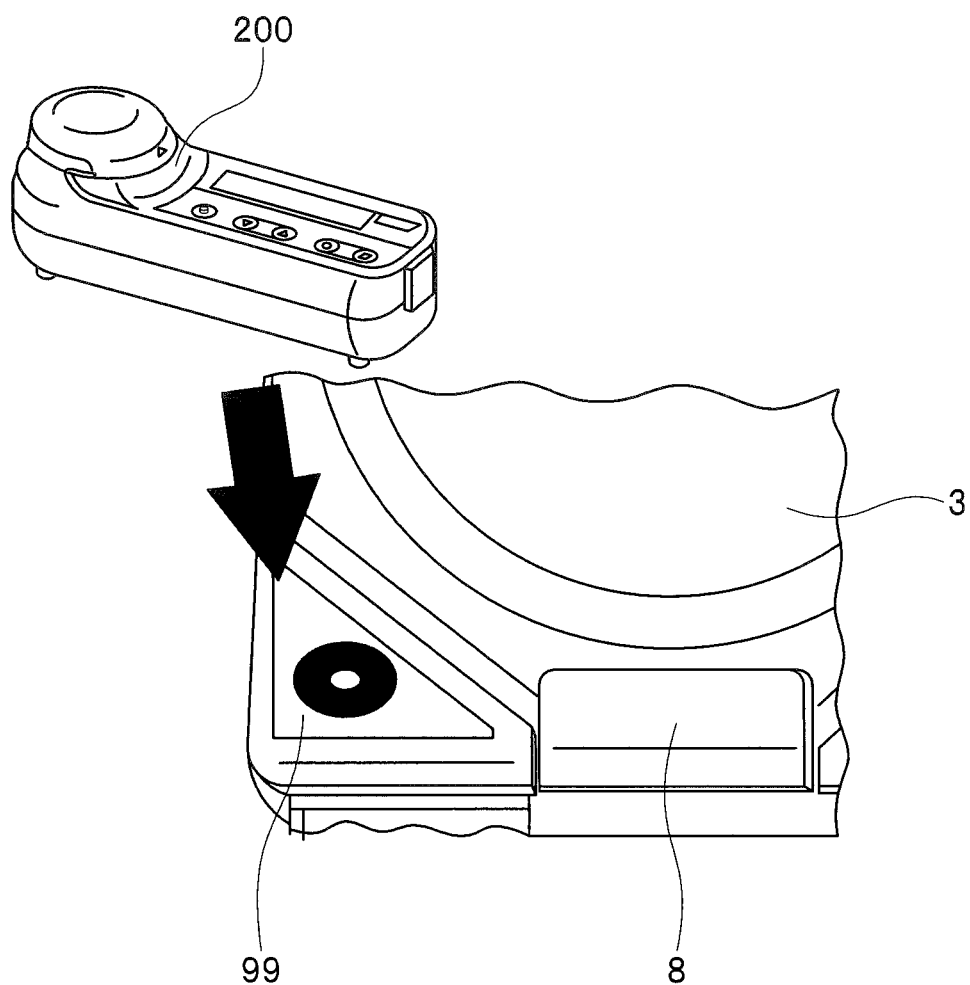
FIG. 5 is a view illustrating one example of the external apparatus shown in FIG. 4, together with a receiving portion of the endoscope cleaning/disinfecting apparatus.

Hereunder, a modification is described using FIG. 4 and FIG. 5. FIG. 4 is a view that schematically illustrates a modification of the configuration of the endoscope cleaning/disinfecting apparatus in which detection of the concentration of a disinfectant solution is performed by an external apparatus, and the detected concentration is inputted to the comparison portion from the external apparatus. FIG. 5 is a view illustrating one example of the external apparatus shown in FIG. 4, together with a receiving portion of the endoscope cleaning/disinfecting apparatus.

In the present embodiment that is described above, a configuration is described in which the concentration detection portion 74 that detects a concentration of the disinfectant solution M and that is connected to the comparison portion 75 is provided in the medicinal solution tank 58, and the concentration of the disinfectant solution M is inputted through the concentration detection portion 74 to the comparison portion 75.

The endoscope cleaning/disinfecting apparatus 1 of the present invention is not limited to the above configuration, and as shown in FIG. 4, a configuration may also be adopted in which the concentration detection portion 74 is not provided in the endoscope cleaning/disinfecting apparatus 1, and instead the concentration of the disinfectant solution M that is sampled from any one of the endoscope housing portion 4, the medicinal solution recovery conduit 61, the medicinal solution conduit 64 and the medicinal solution tank 58 is measured by an external apparatus 200, and the concentration of the disinfectant solution M is inputted from the external apparatus 200 to the comparison portion 75.

Figure 14:
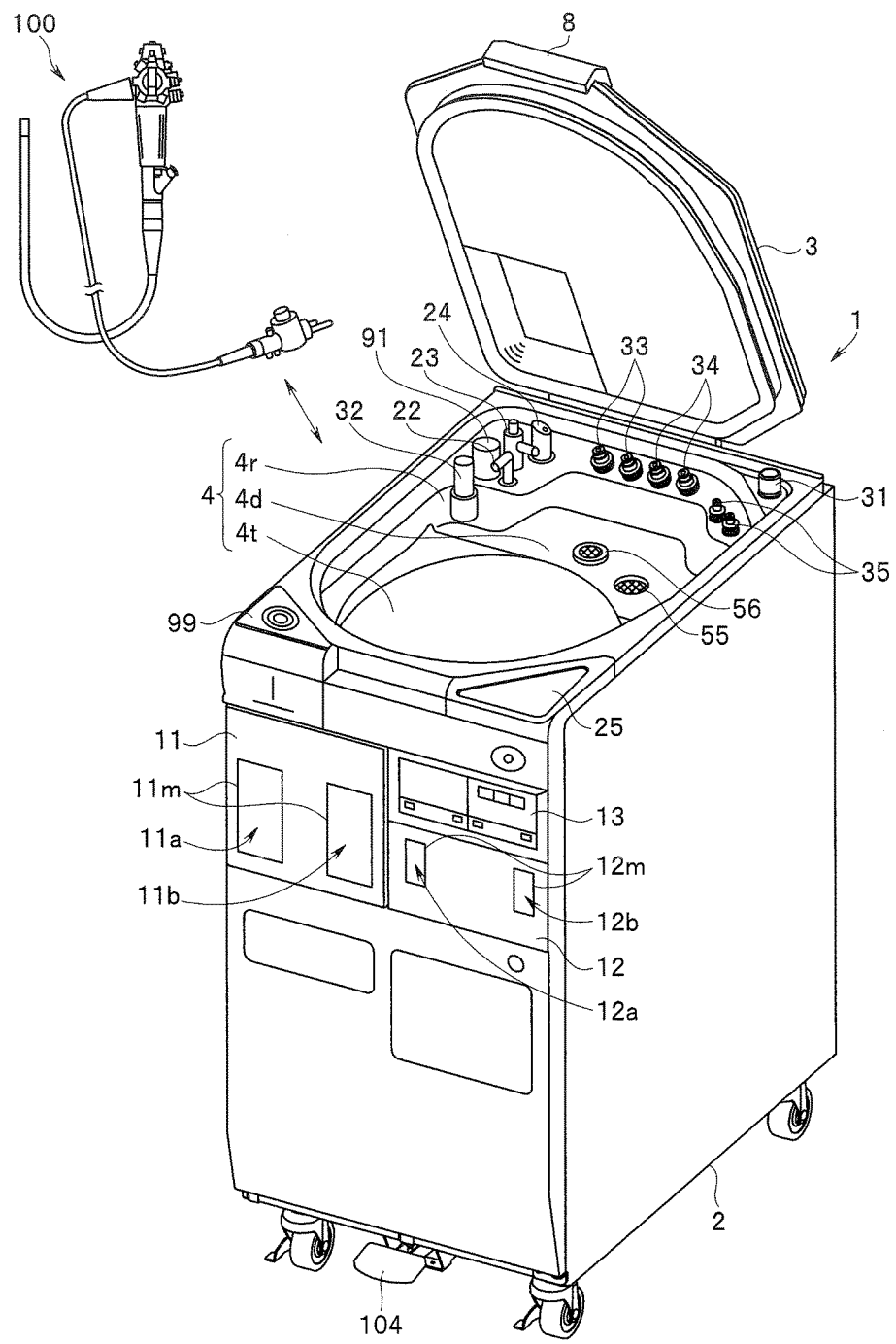
FIG. 14 is a perspective view of an endoscope cleaning/disinfecting apparatus that illustrates one example of the endoscope cleaning/disinfecting apparatus in FIG. 1 in a state in which a top cover is open and an endoscope can be housed in a cleaning/disinfecting tank.

Note that, an absorptiometer as shown in FIG. 5 or the like may be mentioned as an example of the external apparatus 200. Further, as shown in FIG. 5, inputting of a concentration to the comparison portion 75 from the external apparatus 200 may be performed wirelessly by bringing the external apparatus 200 close to a receiving portion 99 constituted by, for example, an RFID, that is provided in the endoscope cleaning/disinfecting apparatus 1. In a case where the external apparatus 200 is connected by wire to the endoscope cleaning/disinfecting apparatus 1, the destination of the wire connection is the receiving portion 99. In addition, in a case where the receiving portion 99 is a main operation panel 25 or a sub-operation panel 13 that are illustrated in FIG. 14, a numerical value of the concentration of the disinfectant solution M measured by the external apparatus 200 may be manually inputted to the comparison portion 75 by the operator.

Further, with respect to the various kinds of driving control of the control portion 70 when detecting the concentration of the disinfectant solution M in the configuration shown in FIG. 4, in the flowchart shown in FIG. 3, only detection of the concentration of the disinfectant solution M by the concentration detection portion 74 in step S1 is replaced by inputting of the concentration by the external apparatus 200, and the remaining steps S2 to step S9 are the same.

Note that the remaining configuration is same as that in the present embodiment that is described above. Further, similar effects as in the present embodiment that is described above can also be obtained by the foregoing configuration in which the concentration of the disinfectant solution M is inputted to the comparison portion 75 by the external apparatus 200.

Figure 6:
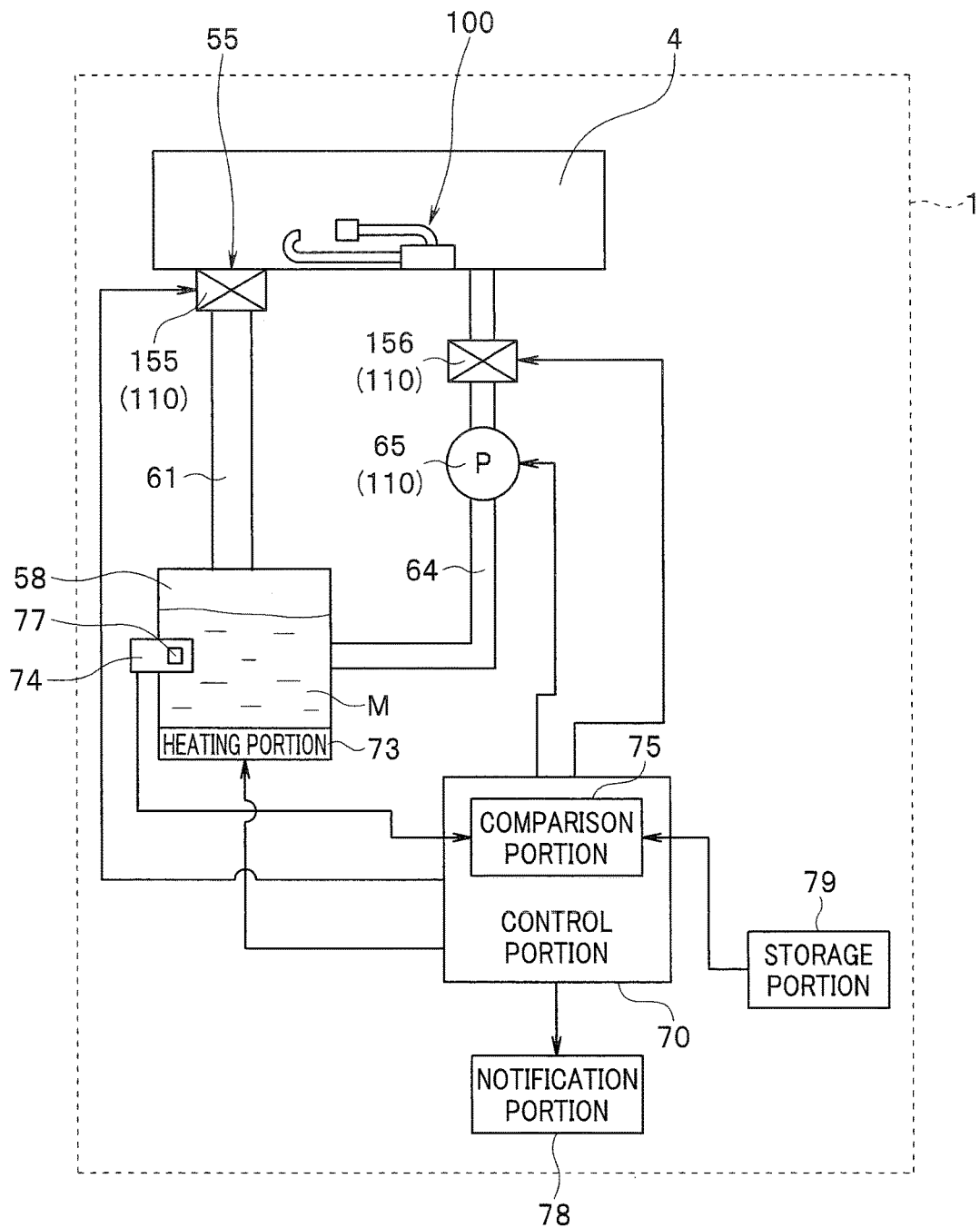
FIG. 6 is a view that schematically illustrates a modification with respect to the endoscope cleaning/disinfecting apparatus shown in FIG. 1, in which an internal pressure regulating valve is provided in a medicinal solution conduit.

Another modification will now be described using FIG. 6 and FIG. 7. FIG. 6 is a view that schematically illustrates a modification in which, with respect to the endoscope cleaning/disinfecting apparatus shown in FIG. 1, an internal pressure regulating valve is provided in the medicinal solution conduit. FIG. 7 is a chart showing disinfecting parameters that are stored in a storage portion of the endoscope cleaning/disinfecting apparatus shown in FIG. 6.

Figure 8:
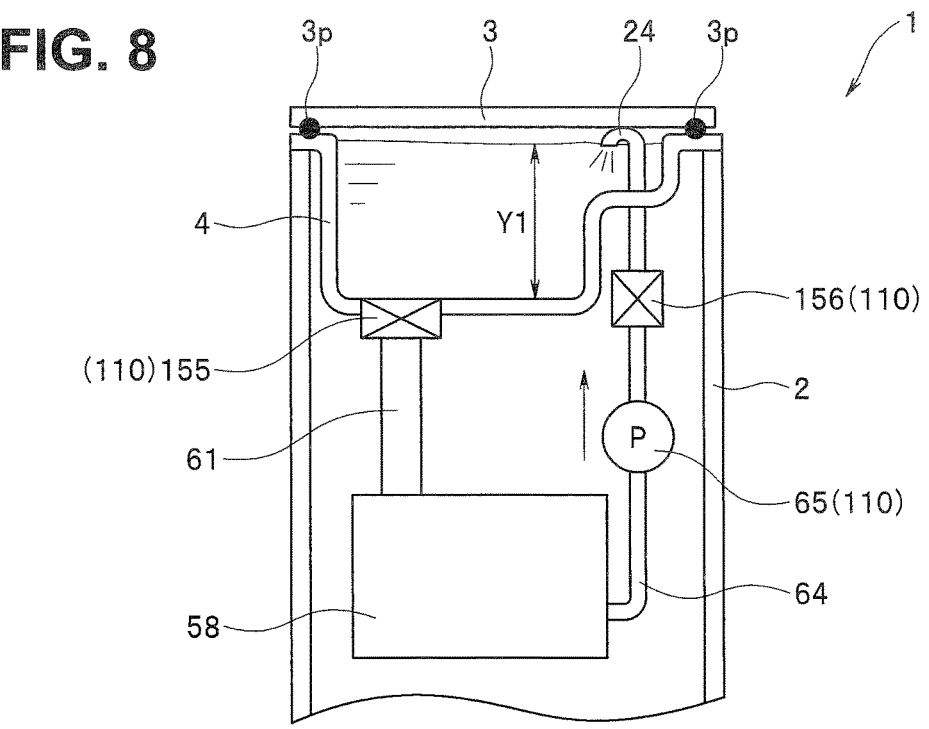
FIG. 8 is a view that schematically illustrates a state in which a valve element of a discharge port shown in FIG. 6 is closed and an internal pressure regulating valve is opened, and a medicinal solution transfer portion is driven to supply a medicinal solution to an endoscope housing portion up to a first water level.
Figure 9:
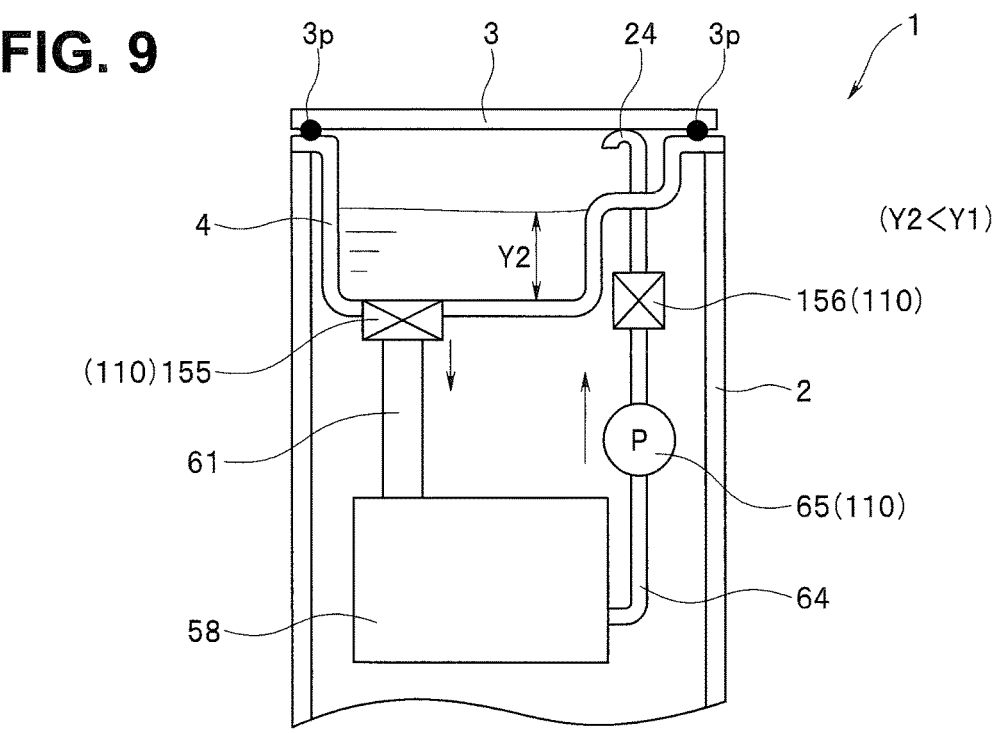
FIG. 9 is a view that schematically illustrates a state in which a valve element of a discharge port shown in FIG. 8 is opened and an internal pressure regulating valve is closed, and a medicinal solution transfer portion is driven to lower the amount of medicinal solution in the endoscope housing portion to a second water level and depressurize the inside of the endoscope housing portion.

Further, FIG. 8 is a view that schematically illustrates a state in which the valve element of the discharge port shown in FIG. 6 is closed and the internal pressure regulating valve is opened, and the medicinal solution transfer portion is driven to supply a medicinal solution to the endoscope housing portion up to a first water level. FIG. 9 is a view that schematically illustrates a state in which the valve element of the discharge port shown in FIG. 8 is opened and the internal pressure regulating valve is closed, and the medicinal solution transfer portion is driven to lower the amount of medicinal solution in the endoscope housing portion as far as a second water level and depressurize the inside of the endoscope housing portion.

In the present embodiment that is described above, a configuration is described in which the first adjustment portion that increases the reaction rate of the disinfectant solution is the heating portion 73 that raises the temperature of the disinfectant solution to a predetermined temperature.

However, the present invention is not limited to the above configuration and, as shown in FIG. 6, the first adjustment portion may be constituted by an internal pressure regulating portion 110 that reduces the internal pressure inside the endoscope housing portion 4 that is in an airtight state in which the endoscope housing portion 4 is airtightly sealed by closing a top cover 3 on an apparatus main body 2 that is described later of the endoscope cleaning/disinfecting apparatus 1.

The internal pressure regulating portion 110 is connected to the control portion 70, and depressurizes the inside of the endoscope housing portion 4 based on driving control of the control portion 70.

Specifically, as shown in FIG. 6, the internal pressure regulating portion 110 includes the valve element 155, the medicinal solution transfer portion 65 and an internal pressure regulating valve 156 that is provided in the medicinal solution conduit 64.

Further, in the present configuration, disinfecting parameters of the disinfectant solution M that are shown in FIG. 7 are stored inside the storage portion 79.

Specifically, as shown in FIG. 7, the disinfecting parameters include: first effect parameters which are the first reference concentration (effective concentration lower limit) B ppm, an air pressure inside the endoscope housing portion 4 that is normal pressure, the temperature D° C., and the immersion time Fmin; and second effect parameters which are the second reference concentration (effective concentration lower limit) C ppm (C<B), an air pressure inside the endoscope housing portion 4 which is a pressure that is reduced by an amount Hhp from normal pressure, the temperature D° C., and the immersion time Fmin.

Note that, the remaining configuration of the endoscope cleaning/disinfecting apparatus 1 is the same as in the present embodiment.

According to the configuration, as shown in FIG. 3, in a case where it is determined in step S5 that the detected concentration of the disinfectant solution M is equal to or greater than C, the control portion 70 executes driving control of the internal pressure regulating portion 110 in step S6.

Specifically, as shown in FIG. 8, in a state in which the top cover 3 is closed via a watertight and airtight member 3p so that the endoscope housing portion 4 is hermetically sealed with respect to the apparatus main body 2 of the endoscope cleaning/disinfecting apparatus 1, the control portion 70 performs control that closes the valve element 155 and control that opens the internal pressure regulating valve 156, and subsequently performs control that drives the medicinal solution transfer portion 65 so that a medicinal solution M inside the medicinal solution tank 58 is supplied to the endoscope housing portion 4 up to a first water level Y1.

Thereafter, as shown in FIG. 9, the control portion 70 performs control to close the internal pressure regulating valve 156, and also performs control to open the valve element 155 and control to drive the medicinal solution transfer portion 65 so that the water level of the medicinal solution M inside the endoscope housing portion 4 falls to a second water level Y2 that is lower than the first water level Y1 (Y2<Y1).

Note that, at the second water level Y2 also, the entire endoscope 100 remains immersed in the medicinal solution M. As a result, the endoscope housing portion 4 is depressurized.

By this means, in the disinfection process in step S8, because the motion of disinfectant solution molecules becomes vigorous, the disinfectant solution M penetrates into every hole and corner of the endoscope 100 that is immersed in the endoscope housing portion 4 and the medicinal efficacy of the disinfectant solution M is thereby improved, and thus a medicinal efficacy that is equal to that of the first effect parameters can be secured.

Hence, similarly to the present embodiment, the life of the disinfectant solution M can be prolonged by temporarily using the disinfectant solution M having the concentration C ppm that is lower than B ppm. Note that, the other advantageous effects are the same as in the present embodiment that is described above.

Figure 10:
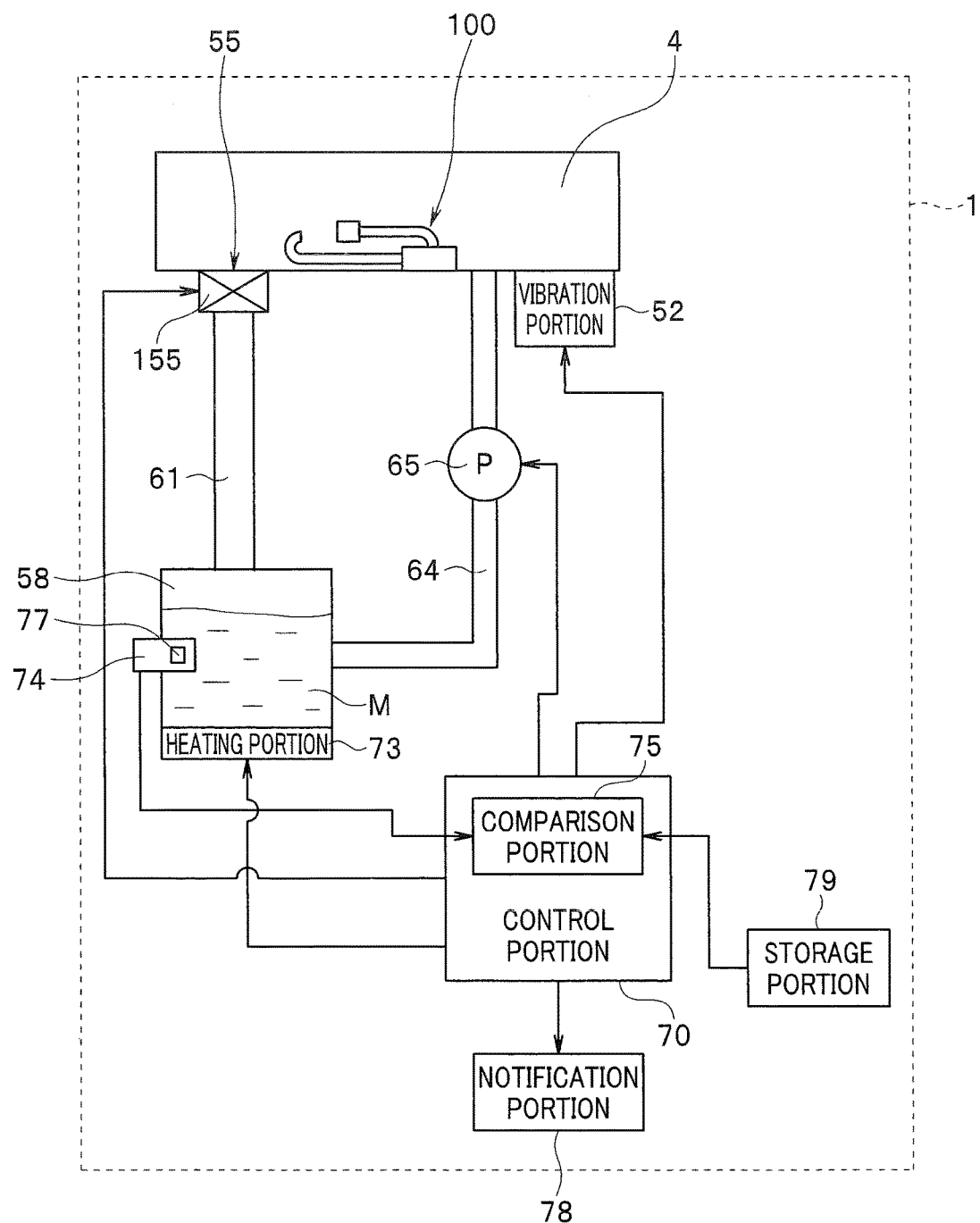
FIG. 10 is a view that schematically illustrates a modification with respect to the endoscope cleaning/disinfecting apparatus shown in FIG. 1, in which a first adjustment portion is constituted by a vibration portion.

A different modification will now be described using FIG. 10 and FIG. 11. FIG. 10 is a view that schematically illustrates a modification in which, with respect to the endoscope cleaning/disinfecting apparatus shown in FIG. 1, the first adjustment portion is constituted by a vibration portion. FIG. 11 is a chart showing disinfecting parameters that are stored in a storage portion of the endoscope cleaning/disinfecting apparatus shown in FIG. 10.

In the present embodiment that is described above, a configuration is adopted in which the first adjustment portion that increases the reaction rate of the disinfectant solution is the heating portion 73 that raises the temperature of the disinfectant solution to a predetermined temperature.

However, the present invention is not limited to the above configuration and, as shown in FIG. 10, the first adjustment portion may be constituted by a vibration portion 52 that causes the disinfectant solution to vibrate within the endoscope housing portion 4. Note that the vibration portion 52 may be constituted by, for example, an ultrasound transducer that is provided in the endoscope housing portion 4.

Further, the vibration portion 52 is connected to the control portion 70 and, by vibrating based on driving control of the control portion 70, causes the disinfectant solution within the endoscope housing portion 4 to vibrate.

In the present configuration, disinfecting parameters of the disinfectant solution M that are shown in FIG. 11 are stored in the storage portion 79.

Specifically, as shown in FIG. 11, the disinfecting parameters include: first effect parameters which are the first reference concentration (effective concentration lower limit) B ppm, no vibrating of the disinfectant solution M, the temperature D° C., and the immersion time Fmin; and second effect parameters which are the second reference concentration (effective concentration lower limit) C ppm (C<B), application of vibrations from the vibration portion 52 to the disinfectant solution M, the temperature D° C., and the immersion time Fmin.

Note that, the remaining configuration of the endoscope cleaning/disinfecting apparatus 1 is the same as in the present embodiment.

According to the configuration, as shown in FIG. 3, in a case where it is determined in step S5 that the detected concentration of the disinfectant solution M is equal to or greater than C, the control portion 70 executes driving control of the vibration portion 52 in step S6.

As a result, in the disinfection process in step S8, when the disinfectant solution M is supplied to the endoscope housing portion 4, because the motion of disinfectant solution molecules becomes vigorous, the disinfectant solution M penetrates into every hole and corner of the endoscope 100 that is immersed in the endoscope housing portion 4 and the medicinal efficacy of the disinfectant solution M is thereby improved, and thus a medicinal efficacy that is equal to that of the first effect parameters can be secured.

Hence, similarly to the present embodiment, the life of the disinfectant solution M can be prolonged by temporarily using the disinfectant solution M having the concentration C ppm that is lower than B ppm. Note that, the other advantageous effects are the same as in the present embodiment that is described above.

Another different modification will now be described hereunder. As described above, in some cases the disinfectant solution M is a solution that undergoes natural deterioration. At such time, not only the concentration, but also the pH value changes from an initial state.

In this case, a pH adjuster may be added to the disinfectant solution M. By doing so, the disinfectant solution M can be returned to the optimal pH value for disinfecting the endoscope 100.

Second Embodiment

FIG. 12 is a chart showing disinfecting parameters that are stored in a storage portion of an endoscope cleaning/disinfecting apparatus of the present embodiment.

A difference in the configuration of the endoscope cleaning/disinfecting apparatus of the second embodiment relative to the configuration of the endoscope cleaning/disinfecting apparatus of the first embodiment illustrated in FIG. 1 and FIG. 2 is that different driving control is performed by the control portion when the comparison portion determines that the medicinal solution concentration is lower than the first reference concentration.

Hence, in the second embodiment, components that are the same as in the first embodiment are denoted by the same reference numerals, and a description of such components is omitted.

In the endoscope cleaning/disinfecting apparatus 1 of the present embodiment, as shown in FIG. 1, the valve element 155 of the discharge port 55 constitutes a second adjustment portion that adjusts a contact time period in which the disinfectant solution M comes in contact with the endoscope 100 in the endoscope housing portion 4.

The disinfecting parameters of the disinfectant solution M shown in FIG. 12 are stored in the storage portion 79.

Specifically, as shown in FIG. 12, the disinfecting parameters include: first effect parameters which are the first reference concentration (effective concentration lower limit) B ppm, an immersion time of Fmin, and the temperature D° C.; and second effect parameters which are the second reference concentration (effective concentration lower limit) C ppm (C<B), an immersion time in the disinfectant solution M of G min that is longer than Fmin (G>F), and the temperature D° C.

In addition, in a case where the comparison portion 75 determines that the concentration of the disinfectant solution M is lower than the first reference concentration B ppm, the control portion 70 performs control to drive the valve element 155, that is, to adjust a time period in which the valve element 155 is closed. In other words, the control portion 70 performs control to adjust a time at which to open the valve element 155 that is in a closed state to extend the contact time period during which the disinfectant solution M contacts the endoscope 100 by a predetermined time period, specifically, from Fmin to G min.

Note that the remaining configuration of the endoscope cleaning/disinfecting apparatus 1 is the same as in the above described first embodiment.

Figure 13:
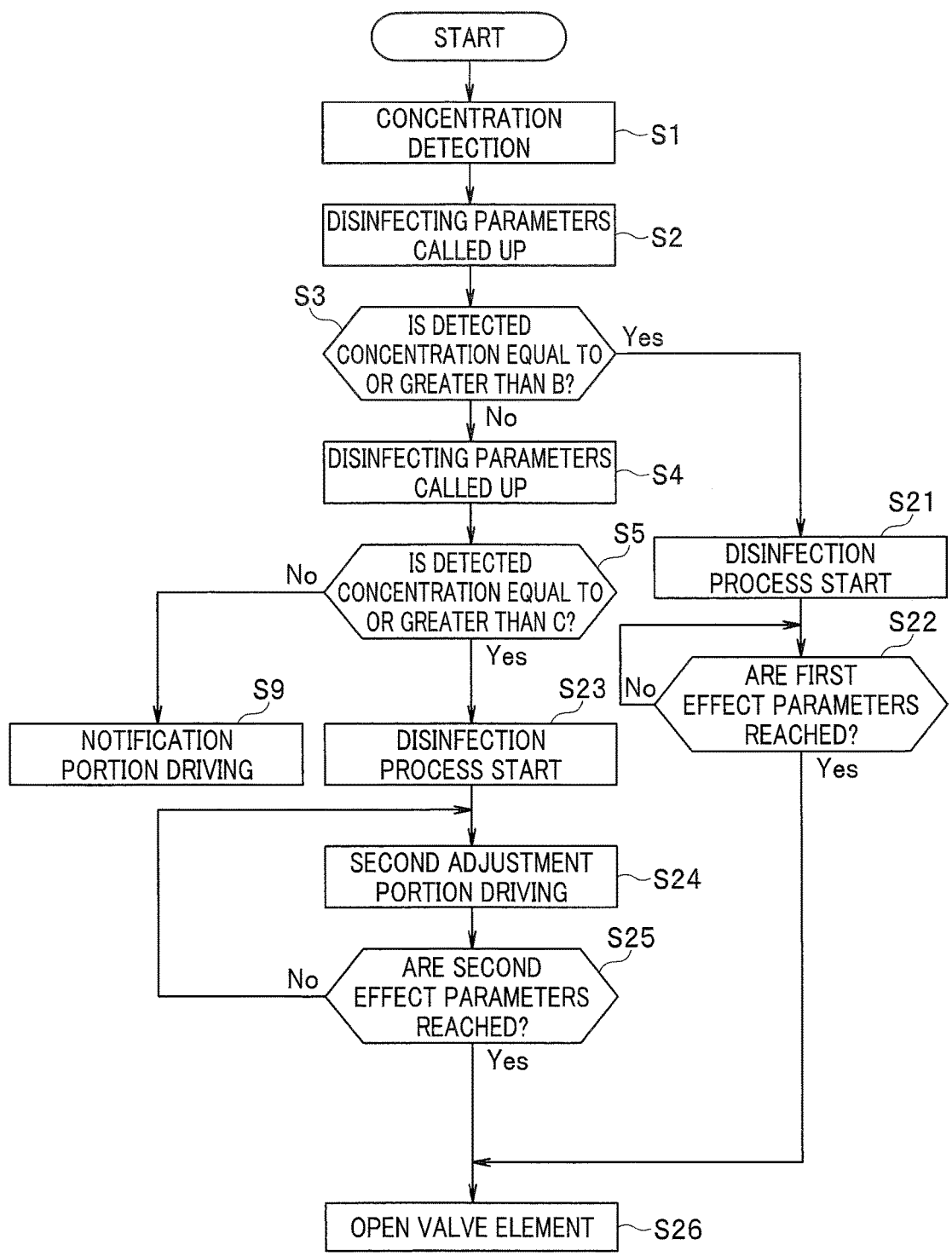
FIG. 13 is a flowchart illustrating various kinds of driving control executed by a control portion when detecting a concentration of a disinfectant solution in the endoscope cleaning/disinfecting apparatus of the second embodiment.

Next, operations in the present embodiment are described using FIG. 13. FIG. 13 is a flowchart illustrating various kinds of driving control of the control portion that are executed when detecting the concentration of the disinfectant solution in the endoscope cleaning/disinfecting apparatus of the present embodiment.

First, when performing disinfecting treatment of the endoscope 100 that is housed in the endoscope housing portion 4, as shown in FIG. 13, in step S1 the control portion 70 detects the concentration of the disinfectant solution M using the concentration detection portion 74.

Next, in step S2, the control portion 70 calls up disinfecting parameters from the storage portion 79, and in step S3 the control portion 70 determines whether the detected concentration of the disinfectant solution M is equal to or greater than the first reference concentration B ppm by performing a comparison using the comparison portion 75.

If the detected concentration of the disinfectant solution M is equal to or greater than the first reference concentration B ppm, the control portion 70 branches to step S21 to start the disinfection process as in the above described step S8. Note that, as shown in step S22, the disinfection process that immerses the endoscope 100 in the endoscope housing portion 4 in the disinfectant solution M is performed based on the first effect parameters, that is, at a temperature of D° C. until the time Fmin is reached.

In step S22, if the first effect parameters are reached, the control portion 70 transitions to step S26. In step S26, the control portion 70 performs control to open the valve element 151, and recovers the disinfectant solution M from the endoscope housing portion 4 into the medicinal solution tank 58 via the discharge port 55 and the medicinal solution recovery conduit 61.

Returning to step S3, if the detected concentration of the disinfectant solution M is less than the first reference concentration B ppm, the control portion 70 transitions to step S4 to again call up disinfecting parameters from the storage portion 79.

Subsequently, in step S5, the control portion 70 determines whether the detected concentration of the disinfectant solution M is equal to or greater than the second reference concentration C ppm by performing a comparison using the comparison portion 75.

If the detected concentration of the disinfectant solution M is less than the second reference concentration C, the control portion 70 branches to step S9. In step S9, on the basis that the disinfectant solution M has no medicinal efficacy, the control portion 70 executes driving control of the notification portion 78 to prompt the operator to replace the disinfectant solution M. Note that, at this time, the control portion 70 may also perform control that stops operation of the endoscope cleaning/disinfecting apparatus 1.

If the detected concentration of the disinfectant solution M is equal to or greater than the second reference concentration C, the control portion 70 transitions to step S23 and starts a disinfection process as in the above described steps S8 and S20. Subsequently, in step S24, the control portion 70 performs control to drive the second adjustment portion, specifically, control that closes the valve element 151 until reaching the second effect parameters.

Note that the control that closes the valve element 151, that is, the disinfection process in step S23 that immerses the endoscope 100 in the endoscope housing portion 4 in the disinfectant solution M is performed, as shown in step S25, at D° C. until the second effect parameters are reached, that is, until reaching the time Gmin.

In step S25, upon reaching the second effect parameters, the control portion 70 transitions to step S26 in which the control portion 70 performs control that opens the valve element 151 and thereby recovers the disinfectant solution M from the endoscope housing portion 4 into the medicinal solution tank 58 through the discharge port 55 and the medicinal solution recovery conduit 61.

Note that, checking of the concentration of the disinfectant solution M by the control portion 70 illustrated in FIG. 13 that is described above is performed each time a disinfection process is performed on the endoscope 100.

Thus, in the present embodiment, in a case where the comparison portion 75 determines that the concentration of the disinfectant solution M is lower than the first reference concentration B ppm, the control portion 70 adjusts a time period in which the valve element 155 is closed. In other words, the control portion 70 performs control to adjust a time at which to open the valve element 155 that is in a closed state to extend the contact time period for which the disinfectant solution M contacts the endoscope 100 by a predetermined time period, specifically, from Fmin to Gmin.

By this means, although conventionally it would be necessary to perform an operation to replace the disinfectant solution M in a case where the concentration of the disinfectant solution M is less than B ppm, according to the present embodiment, by the control portion 70 executing control to extend the contact time period during which the disinfectant solution M contacts the endoscope 100 in the endoscope housing portion 4 to Gmin and thereby satisfy the second effect parameters, the life of the disinfectant solution M can be prolonged by temporarily using the disinfectant solution M having the concentration C ppm that is lower than B ppm without lowering the medicinal efficacy of the disinfectant solution M, and hence the operator can perform an operation to replace the disinfectant solution M at a favorable timing in terms of work efficiency.

Hence, in the present embodiment, by adjusting the immersion time of the endoscope 100 in the disinfectant solution, similar advantageous effects as in the above described first embodiment can be obtained.

Note that, in the present embodiment also, as shown in the above described FIG. 4, a configuration may be adopted in which the concentration detection portion 74 is not provided in the endoscope cleaning/disinfecting apparatus 1, and instead the concentration of the disinfectant solution M that is sampled from any one of the endoscope housing portion 4, the medicinal solution recovery conduit 61, the medicinal solution conduit 64 and the medicinal solution tank 58 is measured by the external apparatus 200, and the concentration of the disinfectant solution M is then inputted to the comparison portion 75 from the external apparatus 200.

Next, an example of the configuration of the endoscope cleaning/disinfecting apparatus 1 in the above described first and second embodiments will be described using FIG. 14 and FIG. 15.

FIG. 14 is a perspective view showing one example of the endoscope cleaning/disinfecting apparatus illustrated in FIG. 1, that shows a state in which a top cover is open and an endoscope can be housed in the cleaning/disinfecting tank. FIG. 15 is a partial perspective view illustrating a state in which a disinfectant solution tray shown in FIG. 14 is drawn out and medicinal solution bottles are set in the disinfectant solution tray.

As shown in FIG. 14, the endoscope cleaning/disinfecting apparatus 1 is an apparatus for cleaning and disinfecting the endoscope 100 after use, and includes a principal portion configured by the apparatus main body 2 and the top cover 3 that is connected by, for example, a hinge, that is not shown, to the upper part of the apparatus main body 2 so as to be openable/closable.

In a state in which the top cover 3 is closed on the apparatus main body 2, the apparatus main body 2 and the top cover 3 are fixed, for example, by a latch 8 that is arranged at a position at which the apparatus main body 2 and the top cover 3 face each other.

A detergent/alcohol tray 11 is disposed at the upper part of a left half portion, for example, on the front face in FIG. 14, of the apparatus main body 2 so as to be capable of being drawn out in the forward direction from the apparatus main body 2, the front face being a side which the operator approaches.

The detergent/alcohol tray 11 houses a detergent tank 11a in which a cleaning agent used for cleaning the endoscope 100 is stored, and an alcohol tank 11b in which alcohol used for drying the endoscope 100 after cleaning/disinfecting is stored. The detergent/alcohol tray 11 can be drawn out from the apparatus main body 2 so that the respective tanks 11a and 11b can be set in the detergent/alcohol tray 11.

Note that the detergent/alcohol tray 11 is provided with two window portions 11m through which the operator can confirm the remaining amounts of the cleaning agent and alcohol filled in the respective tanks 11a and 11b.

Figure 15:
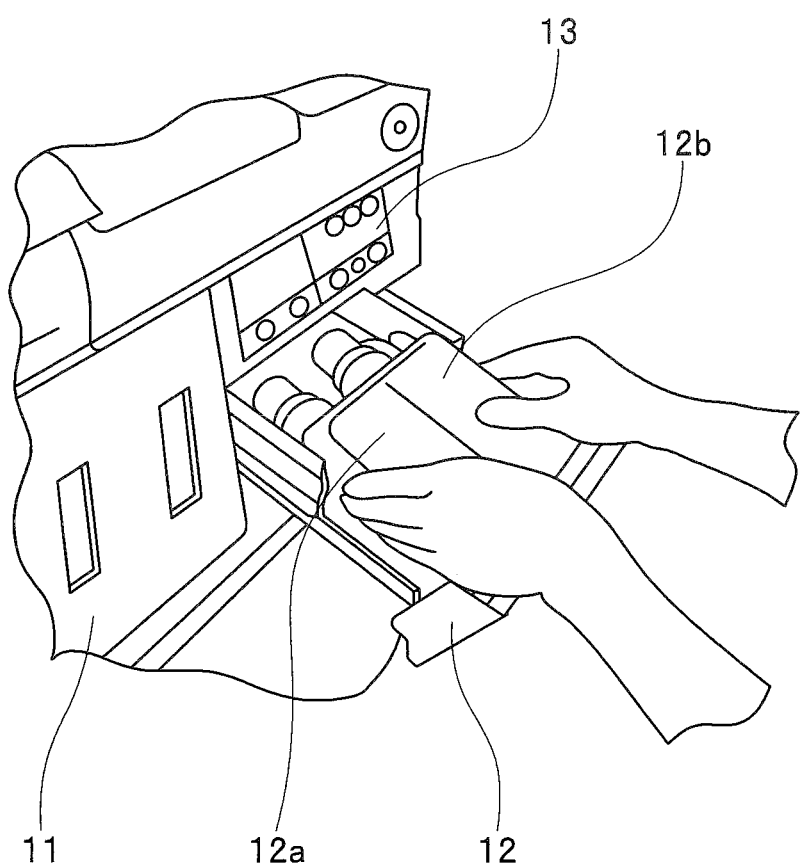
FIG. 15 is a partial perspective view illustrating a state in which a disinfectant solution tray shown in FIG. 14 is drawn out and medicinal solution bottles are set in the disinfectant solution tray.

In addition, as shown in FIG. 15, a disinfectant solution tray 12 is arranged at the upper part of a right half portion, for example, on the front face of the apparatus main body 2 so as to be capable of being drawn out in the forward direction from the apparatus main body 2. For example, a medicinal solution bottle 12a into which a disinfectant solution such as peracetic acid is filled and a medicinal solution bottle 12b into which a buffer agent is filled that are to be used when disinfecting the endoscope 100 are housed in the disinfectant solution tray 12. The disinfectant solution tray 12 can be drawn out from the apparatus main body 2 to allow the two medicinal solution bottles 12a and 12b to be set at predetermined positions.

Note that the disinfectant solution tray 12 is provided with two window portions 12m through which the operator can confirm the remaining amounts of the disinfectant solutions and buffer agent filled in the respective medicinal solution bottles 12a and 12b.

In addition, as shown in FIG. 14, a sub-operation panel 13 on which instruction buttons for displaying a cleaning/disinfecting time and for heating the disinfectant solution are arranged, is arranged above the disinfectant solution tray 12 on the front face of the apparatus main body 2.

Furthermore, a pedal switch 104 is arranged at a lower part on the front face in FIG. 14 of the apparatus main body 2. The pedal switch 104 is provided for causing the top cover 3 that is closed on the upper part of the apparatus main body 2 to open in the upward direction of the apparatus main body 2 when the operator steps on the pedal switch 104.

Further, the apparatus main body 2 includes a main operation panel 25 on the upper surface at, for example, a position that is close to the right end on the front face side which the operator approaches. The main operation panel 25 includes setting switches such as a switch for starting a cleaning/disinfecting operation of the apparatus main body 2 and a cleaning/disinfecting mode selection switch. The apparatus main body 2 also includes, on the upper surface, a receiving portion 99 that is provided at a position close to the left end on the front face side which the operator approaches. The receiving portion 99 is constituted by, for example, an RFID that receives information from the endoscope 100 when the endoscope 100 is brought close to the receiving portion 99.

In addition, a water supply hose connection port 31 is arranged on the upper surface of the apparatus main body 2 so as to be located on a rear face side that opposes the front face which the operator approaches. The water supply hose connection port 31 is connected to a water supply hose, not shown, which is connected to a water tap for supplying tap water to the apparatus main body 2. Note that the water supply hose connection port 31 may be provided with a mesh filter for filtering the tap water.

Furthermore, the endoscope housing portion 4 which can house the endoscope 100 and which has an endoscope housing opening that is opened and closed by the top cover 3 is provided at a substantially center portion of the upper surface of the apparatus main body 2.

The endoscope housing portion 4 is constituted by: a first tank main body 4t that is located on the front face side which the operator approaches; a second tank main body 4d that is located at a position on the rear face side relative to the first tank main body 4t and whose bottom surface is at a lower position than that of the first tank main body 4t; and a terrace portion 4r that is provided around the periphery so as to be continuous with the outer peripheral edge of the endoscope housing opening of the first tank main body 4t and the second tank main body 4d.

When the endoscope 100 is to be cleaned/disinfected after use, the endoscope 100 can be housed in the first tank main body 4t and the second tank main body 4d.

On the bottom surface of the second tank main body 4d are provided: a discharge port 55 for draining from the endoscope housing portion 4 a cleaning liquid, water, alcohol, a disinfectant solution or the like that is supplied to the endoscope housing portion 4; and a circulation port 56 for supplying the cleaning liquid, water, disinfectant solution or the like supplied to the endoscope housing portion 4 to the respective conduits provided inside the endoscope 100 or for resupplying the aforementioned liquids from a water-supply circulation nozzle 24, described later, to the endoscope housing portion 4 through a mesh filter or the like. Note that the circulation port may be provided with a mesh filter that filters the cleaning liquid and the like.

A water level sensor 32 with a cover is provided at an arbitrary position on the side face of the second tank main body 4d. The water level sensor 32 detects the level of a cleaning liquid, water, a disinfectant solution or the like that is supplied to the endoscope housing portion 4.

A detergent nozzle 22 and a disinfectant solution nozzle 23 are provided in the terrace portion 4r. The detergent nozzle 22 is used for supplying the cleaning agent that is diluted to a predetermined concentration with tap water from the detergent tank 11a to the endoscope housing portion 4. The disinfectant solution nozzle 23 is used for supplying the disinfectant solution to the endoscope housing portion 4.

The terrace portion 4r further includes: the water-supply circulation nozzle 24 for supplying water to the endoscope housing portion 4 or for resupplying the cleaning liquid, water, disinfectant solution or the like, which are sucked through the circulation port 56, to the endoscope housing portion 4; and a float switch 91 that detects an abnormal level of the cleaning liquid, water, disinfectant solution or the like that is supplied to the endoscope housing portion 4.

In addition, the terrace portion 4r includes: a plurality, two in this case, of air/water feeding/forceps port connectors 33 for supplying the cleaning liquid, water, alcohol, disinfectant solution or air or the like to an air/water feeding conduit and a suction conduit provided inside the endoscope 100; a plurality, two in this case, of auxiliary water feeding/forceps raising connectors 34 for supplying the cleaning liquid, water, alcohol, disinfectant solution or air or the like to an auxiliary water feeding conduit provided inside the endoscope 100, and a water leakage detection connector 35 for enabling the detection of a water leakage of the endoscope 100.

Figure 16:
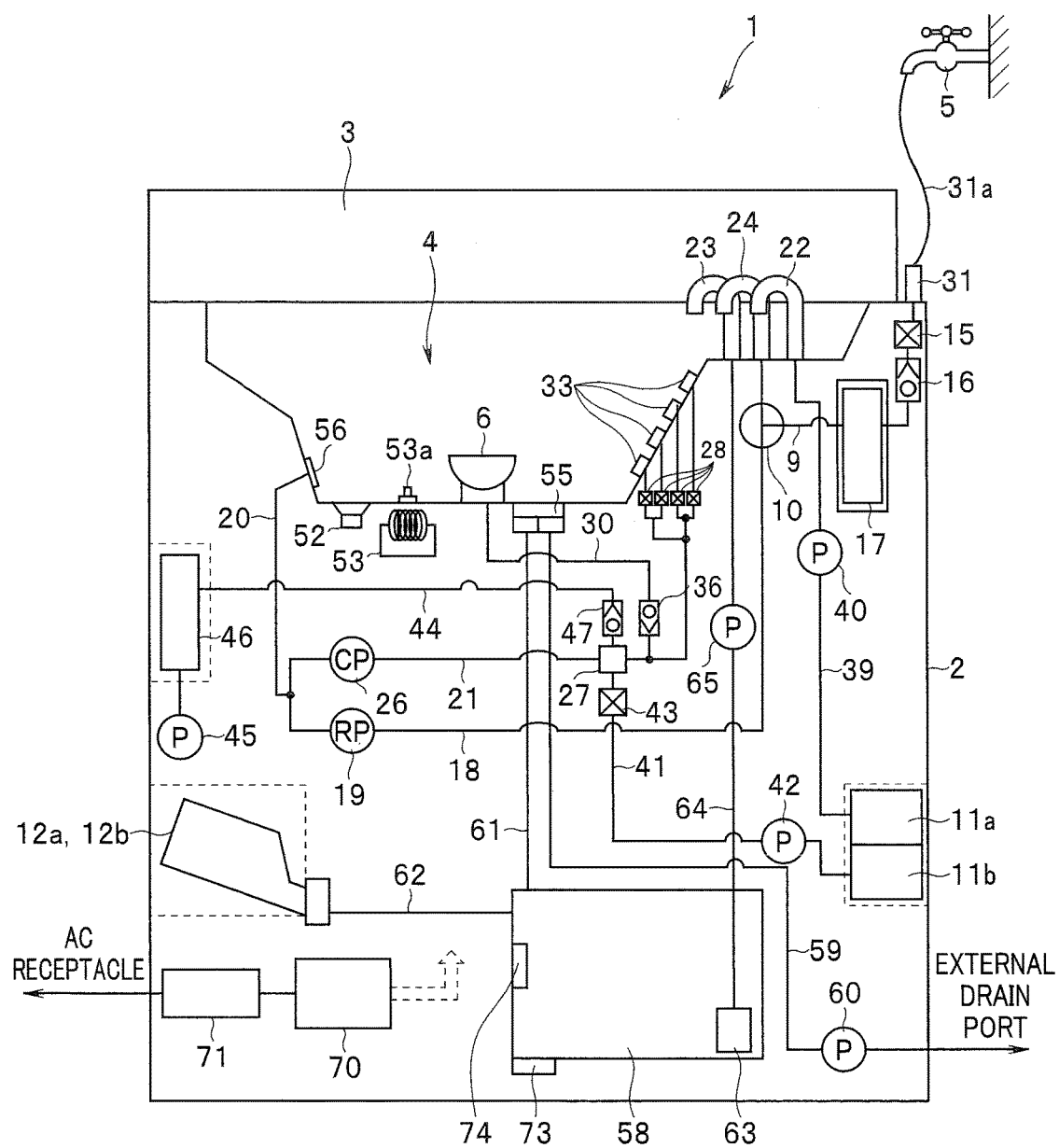
FIG. 16 is a view illustrating an example of the internal configuration of an endoscope cleaning/disinfecting apparatus.

Next, an example of the internal configuration of the endoscope cleaning/disinfecting apparatus shown in FIG. 14 will be described using FIG. 16. FIG. 16 is a view illustrating an example of the internal configuration of the endoscope cleaning/disinfecting apparatus.

As illustrated in FIG. 16, in the endoscope cleaning/disinfecting apparatus 1, the water supply hose connection port 31 to which a water tap 5 is connected through a tube 31a communicates with one end of a water supply conduit 9. The other end of the water supply conduit 9 is connected to a three-way solenoid valve 10. A water supply solenoid valve 15, a check valve 16, and a water supply filter 17 are interposed at positions that are partway along the conduit in that order from the side of the water supply hose connection port 31.

The water supply filter 17 is configured as a cartridge type filtration filter so that the filter can be periodically replaced. The water supply filter 17 removes foreign substances, various germs and the like which are contained in the passing tap water.

The three-way solenoid valve 10 is connected to one end of a liquid flow conduit 18. The three-way solenoid valve 10 uses an internal valve to switch communication with the water-supply circulation nozzle 24 between the water supply conduit 9 and the liquid flow conduit 18. That is, by a switching operation of the three-way solenoid valve 10, the water-supply circulation nozzle 24 communicates with either the water supply conduit 9 or the liquid flow conduit 18. Further, a liquid flow pump 19 that is a non-self-priming pump which can transfer liquid only with an excellent liquid transfer capability is interposed on the other end side of the liquid flow conduit 18.

The circulation port 56 arranged in the endoscope housing portion 4 is connected to one end of a circulation conduit 20. The other end of the circulation conduit 20 branches into two parts which communicate with the other end of the liquid flow conduit 18 and one end of a channel conduit 21. The other end of the channel conduit 21 communicates with the respective connector 33, 34 and 35 (the connector 35 is not illustrated in FIG. 16).

A channel pump 26, a channel block 27 and a channel solenoid valve 28 are respectively interposed in that order, from the one end side, at positions that are partway along the channel conduit 21. The other end of a case conduit 30 that has one end connected to a cleaning case 6 is connected to a portion of the channel conduit 21 between the channel block 27 and the channel solenoid valve 28. A relief valve 36 is interposed along the case conduit 30. Note that the channel pump 26 is constituted of a self-priming pump which can transport both liquid and gas at higher pressures than the non-self-priming pump.

The detergent nozzle 22 is connected to one end of a cleaning agent conduit 39. The other end of the cleaning agent conduit 39 is connected to the detergent tank 11a. A detergent pump 40 is interposed at a position that is partway along the cleaning agent conduit 39. The detergent pump 40 is constituted by a high-pressure self-priming pump for pumping up the cleaning agent from the detergent tank 11a to the endoscope housing portion 4.

The alcohol tank 11b is connected to one end of an alcohol conduit 41. The alcohol conduit 41 is connected to the channel block 27 so as to communicate with the channel conduit 21 as specified.

An alcohol feed pump 42 constituted by a high-pressure self-priming pump for pumping up alcohol from the alcohol tank 11b to the endoscope housing portion 4, and a solenoid valve 43 are interposed along the alcohol conduit 41.

The channel block 27 is also connected to one end of an air conduit 44 so as to communicate with the channel conduit 21 as specified. The air conduit 44 supplies air from an air pump 45 that is constituted by a self-priming pump that can transport gas. The other end of the air conduit 44 is connected to the air pump 45. A check valve 47 and an air filter 46, which is periodically replaced, are interposed at positions that are partway along the air conduit 44.

The above described valve element 155 (not illustrated in FIG. 16) is provided inside the discharge port 55. The valve element 155, not shown, is configured to be openable/closable by a switching operation of a valve so as to discharge cleaning liquid or the like to outside or recover disinfectant solution into the medicinal solution tank 58.

The discharge port 55 is connected to the other end of a drain conduit 59 whose one end is connected to and communicates with an unshown drain hose that is connected to an external drain port. A drain pump 60 constituted by a non-self-priming pump is interposed along the drain conduit 59. The discharge port 55 is also connected to one end of a medicinal solution recovery conduit 61. The other end of the medicinal solution recovery conduit 61 is connected to the medicinal solution tank 58.

The medicinal solution tank 58 is also connected to one end of the medicinal solution supply conduit 62, so that disinfectant solution is supplied to the medicinal solution tank 58 from the medicinal solution bottles 12a and 12b.

The medicinal solution tank 58 houses as specified one end portion of the medicinal solution conduit 64, the one end of which is provided with a suction filter 63. The other end of the medicinal solution conduit 64 is connected to the disinfectant solution nozzle 23. A medicinal solution transfer portion 65 which is constituted by a high-pressure self-priming pump for pumping up the disinfectant solution from the medicinal solution tank 58 to the endoscope housing portion 4 is interposed at a position partway along the medicinal solution conduit 64.

In addition, as described above, the heating portion 73 and the concentration detection portion 74 are provided in the medicinal solution tank 58.

Note that, for example, two of the vibration portions 52 and a heater 53 are arranged in a lower portion of a bottom surface of the endoscope housing portion 4. A temperature detection sensor 53a is also provided at approximately the center of the bottom surface of the endoscope housing portion 4 for thermoregulation of the heater 53.

A power source 71 to which electric power is supplied from an external AC receptacle, and the control portion 70 that is electrically connected to the power source 71 are provided inside the endoscope cleaning/disinfecting apparatus 1.

The control portion 70 receives various signals from the main operation panel 25 and the sub-operation panel 13 (see FIG. 14) that are provided in the endoscope cleaning/disinfecting apparatus 1, and executes driving control of the respective pumps, the respective solenoid valves, the heating portion 73, the notification portion 78 and the like that are described above.

Note that the configuration of the above described endoscope cleaning/disinfecting apparatus illustrated in FIG. 14 to FIG. 16 is merely one example, and the present invention is not limited to this configuration. Further, the endoscope reprocessor is not limited to application to an endoscope cleaning/disinfecting apparatus, and can also be applied to sterilizing apparatus or the like that uses a medicinal solution. In addition, with regard to the medicinal solution also, the present invention can also be applied with respect to a medicinal solution having medicinal efficacy that is other than a disinfectant solution, for example, a sterilizing agent.

What is claimed is:

1. An endoscope reprocessor, comprising:
   an endoscope housing in which an endoscope is housed;
   a medicinal solution tank that is communicated with the endoscope housing and in which a medicinal solution is stored;
   a pump that transfers the medicinal solution from the medicinal solution tank to the endoscope housing;
   a first adjustment portion that increases a reaction rate of the medicinal solution in a state in which a concentration of the medicinal solution is lower than a first reference concentration; and
   a controller comprising hardware, the controller being configured to:
      compare the concentration of the medicinal solution and a second reference concentration that is lower than the first reference concentration; and
      drive the first adjustment portion where the concentration of the medicinal solution is higher than the second reference concentration; and
   a notification portion that produces a warning, wherein in a case where the concentration of the medicinal solution is lower than the second reference concentration, the controller drives the notification portion;
   wherein the first adjustment portion comprises one of a heater that raises a temperature of the medicinal solution to a predetermined temperature, a vibrator that causes the medicinal solution to vibrate inside the endoscope housing or an internal pressure regulator that reduces an internal pressure of the endoscope housing in an airtight state.

2. The endoscope reprocessor according to claim 1, further comprising:
   a concentration detector that detects a concentration of the medicinal solution and inputs the concentration of the medicinal solution to the controller.

3. The endoscope reprocessor according to claim 1, wherein the controller is further configured to receive information regarding a concentration of the medicinal solution that is inputted from an external apparatus that detects the concentration of the medicinal solution.

* * * * *